United States Patent [19] [11] 4,178,938
Au [45] Dec. 18, 1979

[54] PRESSURE CONTROL SYSTEMS

[76] Inventor: Anthony S. Au, P.O. Box 2593, Station A, Sudbury, Ontario, Canada, P3A 4S9

[21] Appl. No.: 809,802

[22] Filed: Jun. 24, 1977

[51] Int. Cl.² ............................................ A61M 25/00
[52] U.S. Cl. .............................. 128/207.15; 251/61.1
[58] Field of Search ............ 128/351, 349 B, 349 BV, 128/344, 208, 342, 2.05 S; 251/61.1

[56] References Cited

U.S. PATENT DOCUMENTS

| 2,990,252 | 6/1961 | Geldern et al. | 251/61.1 X |
| 3,064,935 | 11/1962 | Collins | 251/61.1 |
| 3,502,297 | 3/1970 | Wardrup | 251/61.1 X |
| 3,504,676 | 4/1970 | Lomholt | 128/351 |
| 3,693,611 | 9/1972 | Ploss | 251/61.1 X |
| 4,005,701 | 2/1977 | Aisenberg et al. | 128/2.05 S |

FOREIGN PATENT DOCUMENTS 2055049 12/1971 Fed. Rep. of Germany ............ 128/351

Primary Examiner—Henry J. Recla
Attorney, Agent, or Firm—Fetherstonhaugh & Co.

[57] ABSTRACT

A pneumatically controlled pressure relief valve and various systems incorporating a pneumatically controlled pressure relief valve. The valve has a flexible valve closure member which is expandable to close a through passage of the valve and includes a pressure chamber disposed externally of the valve passage and isolated from the through passage by the flexible valve closure member so that the valve may open and close in response to the differential between the pressure in the pressure chamber and the pressure in the through passage of the valve. An input passage opens into the pressure chamber for admitting air and a manually operable valve is provided for opening and closing the input passage to regulate the admission of air. The systems incorporating the valve include an inflatable cuff system for a tracheal or endotracheal tube, a positive end expiratory pressure system and a suction system incorporating a suction catheter.

9 Claims, 14 Drawing Figures

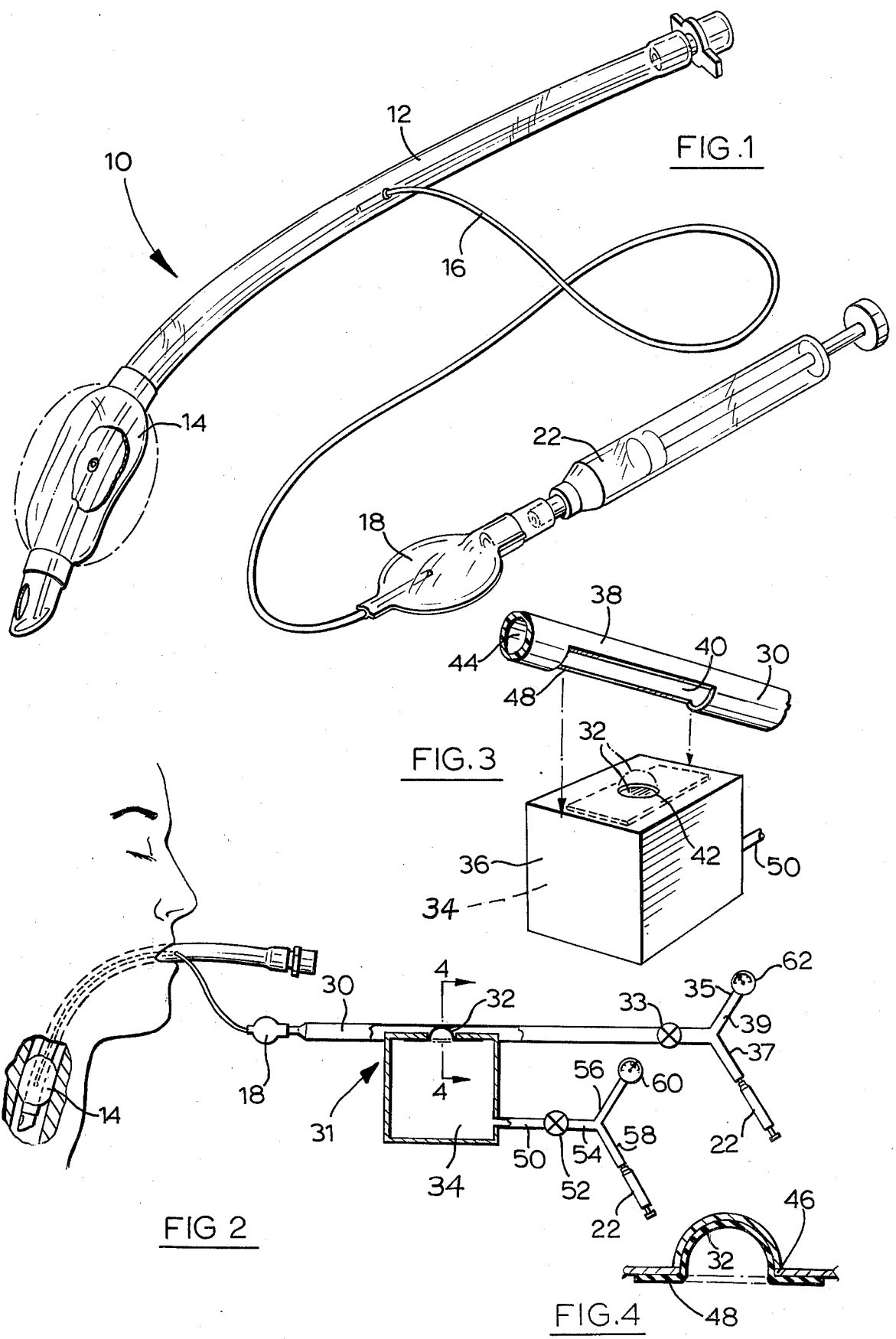

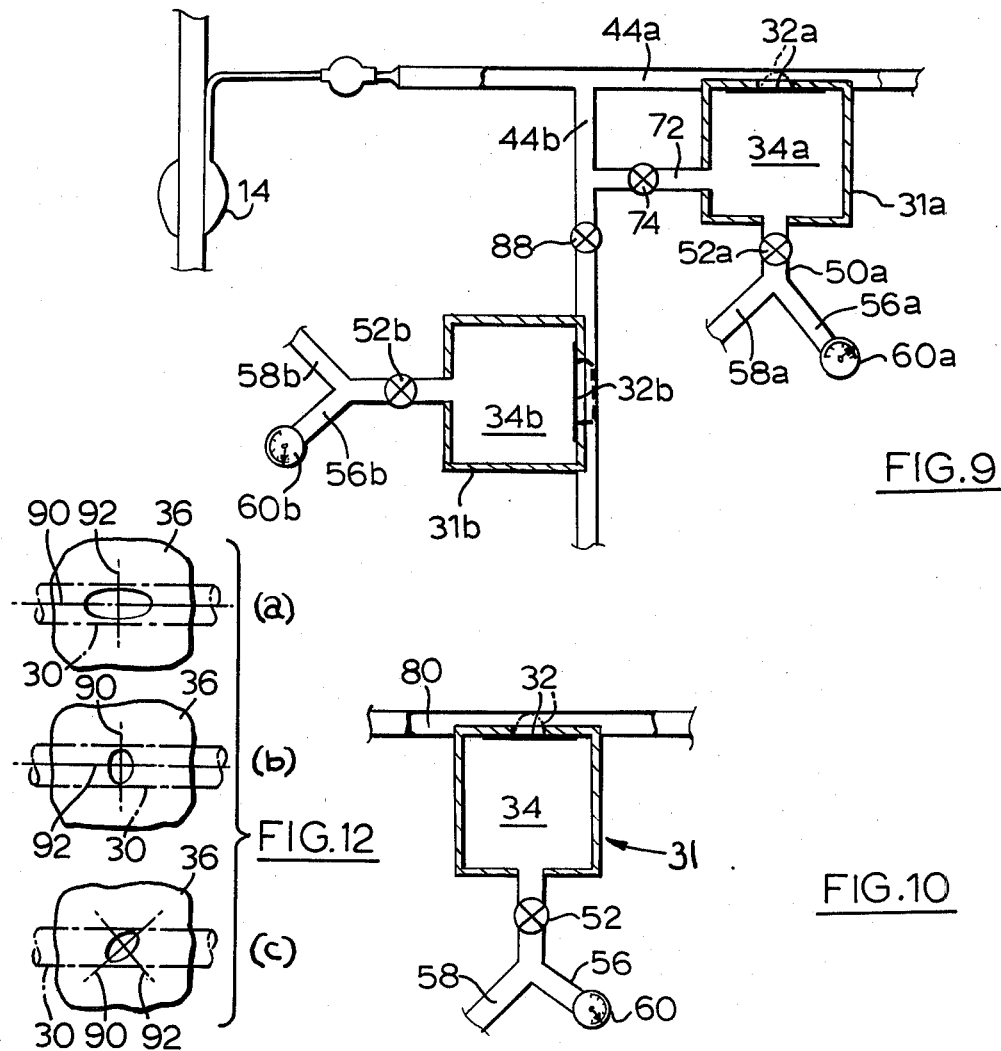
FIG.9
FIG.12
FIG.10
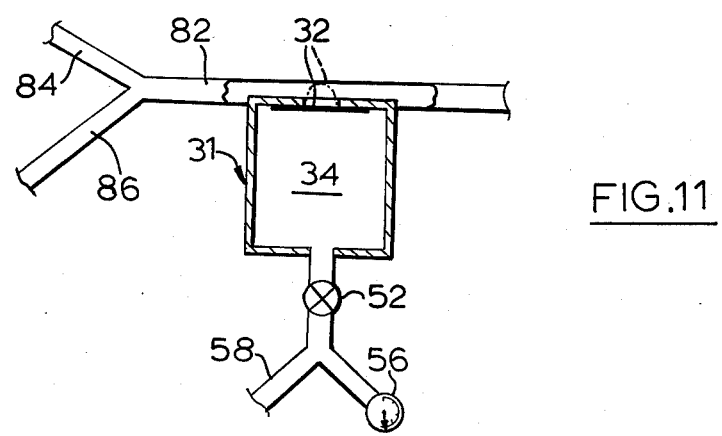
FIG.11

PRESSURE CONTROL SYSTEMS

FIELD OF INVENTION

This invention relates to pneumatically controlled pressure relief valves and systems employing such valves.

In particular, this invention relates to an pneumatically controlled pressure relief valve and an inflatable cuff system of a tracheal, endotracheal or endobronchial tube or the like, a positive end expiratory system, suction system, each of the systems being improved by the use of a pneumatically controlled pressure relief valve.

PRIOR ART

Pneumatic valves which employ a diaphragm for opening and closing a through passage in response to pressure variations in various systems have been known for many years. In most instances, the diaphragm forms the actuating mechanism for actuating a mechanical valve closure member.

A number of special purpose diaphragm control valves have been developed in which the diaphragm member itself is expandable to directly control the flow of fluid through a valve. One such device is illustrated in U.S. Pat. No. 2,598,207, E. G. Bailey et al, dated May 27, 1952. In this device, a bladder is located within a conduit and the bladder is inflatable to restrict the flow of fluid through the conduit. The extent to which the bladder is inflated is determined by pressure within the conduit in use and is controlled by a pressure regulator. The pressure regulator includes a complex system of moving parts which add to its cost and is not compatible with pressure systems such as those employed in medical applications such as the inflation of a cuff of a tracheal or endotracheal tube. The valving system of the Bailey et al patent is particularly adapted for use in industry in that the pressure regulator is of a type commonly used in industry.

In the medical field, tracheal intubation, also known as endotracheal intubation, has always carried with it the risk of tracheal damage. The risk of tracheal damage increases with increased duration of intubation and, more importantly, with an increase in the pressure in the cuff of the tracheal tube. Despite various modifications in the cuffs of tracheal tubes and despite meticulous care in avoiding over-inflation of the cuffs of the tracheal tubes, complications still occur. Previous modifications to tracheal tubes have included the provision of high volume, low pressure cuff systems. However, such systems have not eliminated the tracheal damage problem. One cause of tracheal damage is believed to be the initial high pressure in the cuff of the tracheal tube during the initial inflation of the cuff. Damage can also result in circumstances where the pressure of the cuff is initially quite low but increases during surgery because of diffusion of anaesthetic gases (e.g. nitrous oxide, oxygen and other anaesthetic gases) into the cuff. In circumstances where patients are intubated as, for example, when patients are receiving intensive care, despite meticulous monitoring of their cuff pressures in an intensive care unit prior to surgical operations the cuff pressures may increase during and after their operations as a result of diffusion of gases into the cuffs as described above.

Despite the existence of problems related to tracheal damage resulting from cuff pressure for some considerable time, no simple and effective pressure release system has been proposed for use in such systems. The pneumatic valve of the present invention is particularly suitable for use in an inflatable cuff system of a tracheal intubation or endotracheal intubation system in that it is compatible with such a system and in that the control pressure applied to the pneumatic valve may be applied by a syringe of the type used to inflate the cuff. The valve also lends itself to use with appropriate manometers for measuring the cuff inflation pressure and regulating pressure applied to the valve. The valve may also be readily adapted to provide for a simultaneous inflation of the cuff and pressurizing of the pressure chamber of the valve used to regulate the relief pressure of the valve.

Because an increase in pressure can result in tracheal damage, it is important that any pressure relief valve used in such a system must be extremely sensitive. The pneumatic valve of the present invention employs a pressure chamber of substantial volume so that the diaphragm which closes the valve can be moved to an open position without causing any great increase in pressure in the pressure chamber. For this reason, the capacity of the pressure chamber is preferably several times greater than the increase caused by the expansion of the diaphragm to its position closing the valve.

The pneumatic valve of the present invention is also suitable for use in maintaining a positive end expiratory pressure in treating patients with cardio-pulmonary deseases. The value of a positive end expiratory pressure (P.E.E.P.) in the treatment of patients with cardio-pulmonary deseases has been clearly established. This P.E.E.P. is usually achieved by using valves employing weights or diaphragms and springs or by immersing the expiratory limb of the patient's breathing circuit in water. The problem with the use of weighted valve mechanisms is that their operation may be adversely influenced by a change in position of the valves and, as a result, difficulty is experienced during the transportation of patients. The problem with the use of valves employing diaphragms and springs in combination is that such valves are subject to breakage of the springs and inaccuracy of pressure regulation due to changes in spring elasticity. In addition, such mechanisms are not compatible with medical systems as a whole.

In suction systems in which suction is applied to a suction catheter or the like, it is frequently important to ensure that excessive suction is not applied by the catheter. Again the pneumatic valve of the present invention can be used to advantage in such a system by providing a relief valve which will normally close a vent to atmosphere passage in such a system and which will open to vent the suction system to atmosphere and thereby limit the negative pressure applied by the suction machine to the catheter.

SUMMARY OF INVENTION

According to one aspect of the present invention, there is provided a pneumatic valve which comprises a through passage having an input end and an output end, a valve passage opening into said through passage, a flexible valve closure member mounted at said valve passage, said flexible valve closure member being expandable from a first position permitting free flow of fluid through said passage to a second position closing said through passage, a pressure chamber disposed externally of said valve passage and isolated from said through passage by said flexible valve closure member whereby said flexible valve closure member may be moved between said first and second positions in response to variations in the differential between the pressure in said pressure chamber and the pressure in said through passage, input passage means opening into said pressure chamber for admitting air to and venting air from said pressure chamber, valve means for opening and closing said input passage to regulate the admission of air to and venting of air from said pressure chamber.

According to a further aspect of the present invention, there is provided in an inflatable cuff system of a tracheal or endotracheal tube having an inflation passage communicating with the inflatable cuff, the improvement of a pneumatic valve comprising a pressure chamber, a valve closure member adapted to open and close said inflation passage in response to a pressure differential between said inflation passage and said pressure chamber, input passage means opening into said pressure chamber for admitting air to said pressure chamber to pressurize said chamber to set the pressure at which the valve closure member will open to vent said inflatable cuff system, and means for selectively opening and closing said input passage means.

According to yet another aspect of the present invention there is provided in an expiratory system having an expiratory passage, the improvement of means for generating a positive end expiratory pressure comprising a pneumatic valve comprising a pressure chamber, a valve closure member adapted to open and close said expiratory passage in response to a pressure differential between said expiratory passage and said pressure chamber, input passage means opening into said pressure chamber for admitting air to said pressure chamber to pressurize said chamber to set the pressure at which the valve closure member will open to vent said expiratory system and means for selectively opening and closing said input passage means.

PREFERRED EMBODIMENTS

The invention will be more clearly understood after reference to the following detailed specification read in conjunction with the drawings wherein, FIG. 1 is a pictorial view of a cuffed endotracheal tube system and an inflating syringe of a type in association with which the valve of the present invention may be employed;

FIG. 2 is a diagrammatic illustration of a tracheal tube system incorporating a pneumatic valve according to an embodiment of the present invention;

FIG. 3 is an exploded view of a pneumatic pressure relief valve according to an embodiment of the present invention;

FIG. 4 is a sectional view along the line 4—4 of FIG. 2;

FIGS. 5 through 10 illustrate various systems for charging the pneumatic pressure relief valve and its associated system which is to be vented; and FIG. 11 illustrates a modification in which a pneumatic pressure relief valve is used to control the suction applied to a suction catheter.

FIGS. 12a, 12b and 12c illustrate alternative configurations of the valve passage opening into the through passage of the valve.

Figure 5:
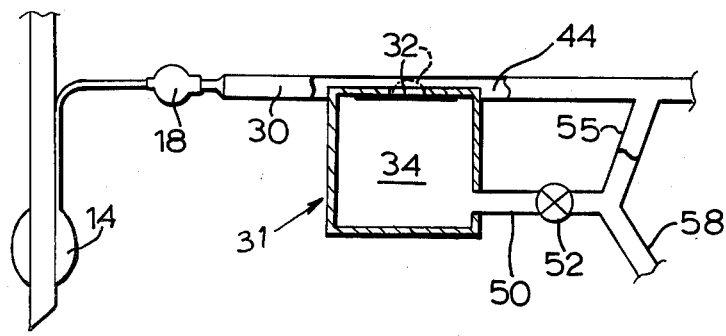

With reference to FIG. 1 of the drawings, the reference numeral 10 refers generally to an assembly which includes a cuffed endotracheal tube and a syringe for inflating the cuff.

The system includes an endotracheal tube 12 which has an inflatable cuff 14 and a cuff inflation tube 16 which extends from the cuff 14 through a portion of the body of the tube 12 to a pilot cuff bladder 18. The pilot cuff bladder 18 is adapted to receive one end of an inflating syringe 22. The cuff 14 can be inflated by operating the inflating syringe 22. When the cuff 14 is inflated, the pilot cuff bladder 18 is also inflated. The pilot cuff bladder 18 provides visible indication that the cuff 14 is inflated.

A pneumatically controlled pressure relief valve constructed in accordance with an embodiment of the present invention and used in association with an endotracheal tube as illustrated in FIG. 2 of the drawings and generally identified by the reference numeral 31.

As shown in FIG. 3 the pressure relief valve 31 comprises a tubular portion 30, a flexible valve closure member 32 and a pressure chamber 34. The tubular member 30 has a semi-circular portion 38 which opens outwardly at 40 from the through passage 44.

The pressure chamber 34 is located within a housing 36 which is formed with a circular valve passage 42 at the upper end thereof. The radius of the circular valve passage 42 corresponds to the radius of the semi-circular portion 38. The housing 36 is proportioned to fit within the recess 48 formed in the tubular member 30. The flexible valve closure member 32 is preferably made from readily extensible flexible diaphragm material which is impermeable to the ambient gas or fluid used in the system to ensure that diffusion of gas or fluid through the diaphragm does not occur. The valve closure member 32 has a peripheral edge portion 48 (FIG. 4) extending around the periphery of the valve passage 42. The valve closure member 32 is extensible from the relaxed position shown in chain lines in FIG. 4 and shown in solid lines in FIG. 3 to the extended position shown in FIG. 4 in which it extends into the through passage 44 of the tubular member to close the through passage 44. The peripheral edge portion 48 of the valve closure member 32 may be adhesively secured or otherwise suitably clamped by a mounting plate to the adjacent side wall of the housing 36 so that the peripheral edge portion is restrained when the central portion of the valve closure member 32 is expanded into the through passage 44.

Air is admitted to the pressure chamber 34 through an input passage 50. In the embodiment shown in FIG. 2, a closure valve 52 is provided which is movable between an open and a closed position for opening and closing the input passage 50 as required in use. A Y-shaped piece 54 is connected to the valve 52 and has passages 56 and 58 opening therethrough. A manometer 60 is connected to the end of the passage 56 and the passage 58 is adapted to receive an inflating syringe 22.

Closure valve 33 is located in the tubular member 30 and is operable to selectively open and close the passage 44 downstream of the flexible valve closure member 32. A Y-piece 39 is located at the end of the tubular member 30 and has passages 35 and 37 opening therethrough.

In use, a manometer is connected to the passage 35 of the Y-piece 39 and an inflating syringe 22 is connected to the passage 37. With the valve 33 in the open position, the cuff of the tracheal tube is inflated by injecting air from the syringe 22 to achieve the required seal. The attending physician is able to determine when the required seal is obtained by auscultation. The pressure reading on the manometer 62 is noted when the required seal is obtained and the syringe 22 is removed from the arm 37. The valve 33 remains in the open position with the result that the cuff is now deflated. A manometer 60 is then connected to the passage 56 of the Y-piece 54 and an inflating syringe 22 is connected to the passage 58. The valve 52 is moved to the open position and the pressure chamber 34 is pressurized by the inflating syringe 22 until the reading on the manometer 60 corresponds to the reading noted on the manometer 62 when the cuff 14 was inflated to the required pressure. If a pressure in excess of the cuff pressure is required, the pressure chamber 34 may be pressurized to the required higher pressure. Such a decision may be made by the attending physician. The valve 52 is then moved to the closed position and the inflating syringe 22 removed. As a result of the pressure applied to the valve closure member 32 by the pressure chamber 34, the valve closure member 32 will move to a position protruding through the opening 42 and closing the through passage 44. Thereafter, the tracheal tube is reinflated by means of inflating syringe 22 connected to the passage 37 as previously described. The inflating syringe 22 and manometer 62 may then be disconnected from passages 37 and 35 respectively so that the through passage 44 of the valve member may vent to atmosphere through the open valve 33 and passages 35 and 37. Thus, if the pressure in the cuff 14 exceeds the pressure in the pressure chamber 34, the valve member 32 will be deflected inwardly to permit venting of the cuff 14 to prevent an excessive build-up of pressure in the cuff 14.

As previously indicated, the capacity of the pressure chamber 34 is substantially greater than the expanded volume of the valve closure member 32 so that the pressure within the pressure chamber 34 will only increase very slightly when the valve closure member 32 is deflected inwardly to permit venting of the cuff and thus only a very slight pressure differential is required between the pressure chamber 34 and the through passage 44 to cause the valve closure member 32 to move to and fro between an open and closed position. Preferably the unexpanded volume of the pressure chamber is at least three times the increase in volume required to close the pressure relief valve.

FIG. 5 of the drawings illustrates a modification in which like numerals are applied to like parts to those illustrated in FIG. 2 of the drawings. In this embodiment, a passage 55 extends between the passage 58 and the through passage 44 on the downstream side of the pressure relief valve. In use, the valve 52 is located in the open position and the outer end of the through passage 44 is occluded manually or by other means. A pressure source such as an inflating syringe is connected to the passage 58 and air is injected under pressure into the cuff 14 by way of passage 55 and through passage 44 and into the pressure chamber 34 by way of passage 50. Air is injected until the pressure in the cuff of the tracheal tube is adequate to achieve a seal between the cuff and the tracheal wall. This is determined clinically as previously described. Both the cuff 14 and chamber 34 are pressurized simultaneously. When the required pressure has been obtained and the system is stabilized, the valve 52 is closed. The pressure source is disconnected from the passage 58 so that the passage 44 may be vented to atmosphere through the passage 55 and passage 58. As a result, a pressure differential is established between the passage 44 and the pressure chamber 34 sufficient to cause the flexible valve closure member 32 to extend to close the through passage 44. The occlusion at the passage 44 may then be removed or may continue so long as the passages 55 and 58 remain open to atmosphere. If and when the pressure in the cuff 14 exceeds the pressure in the pressure chamber 34, the pressure differential will cause the valve member 32 to move to position to permit venting of the cuff 14. To deflate the cuff 14 of the tracheal tube, the valve 52 is opened to vent the pressure chamber 34 and thus cause the valve closure member 32 to return to its relaxed configuration. This structure has the advantage that the end of the tube 44 may be permanently sealed if the passages 55 and 58 remain open to atmosphere. The permanent sealing of the through passage has the advantage of providing compactness and ease of pressurization of the cuff 14 and pressure chamber 34 without the need for a manometer. The possibility of the valve closure member 32 occluding the through passage 44 during the simultaneous pressurization of the cuff and chamber can be prevented by ensuring that the passage 50 has a smaller diameter than the passage 55.

Figure 6:
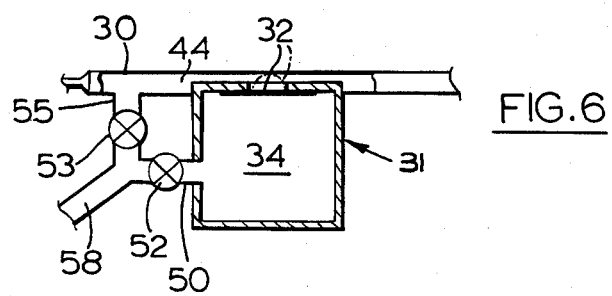

FIG. 6 of the drawings illustrates a further modification in which like numerals are applied to like parts to those illustrated in FIG. 5 of the drawings. In this embodiment, the passage 55 is connected to the through passage 44 on the upstream side of the pressure relief valve and valve 53 is located in the passage 55. In use, the valves 52 and 53 are located in an open position. The free end of the through passage 44 downstream from the pressure relief valve is occluded manually or by other means. A pressure source is connected to the passage 58 and air is introduced until the pressure in the system which is to be pressurized, is adequate. The valves 52 and 53 are then closed and the free end of the through passage 44 is opened. The drop in pressure resulting from the opening of the free end of the through passage 44 may cause a sufficient pressure differential between the through passage 44 and the pressure chamber 34, with the result that the diaphragm 32 will extend to close the through passage 44. If the pressure in the cuff exceeds the pressure in the pressure chamber 34, the diaphragm 32 will be deflected to permit air to escape to atmosphere. This structure has the advantage of being compact and can be operated without the aid of a manometer when pressurizing the cuff system and the pressure chamber. It will, however, be apparent that a manometer may be used in association with the system of the present invention.

Figure 7:
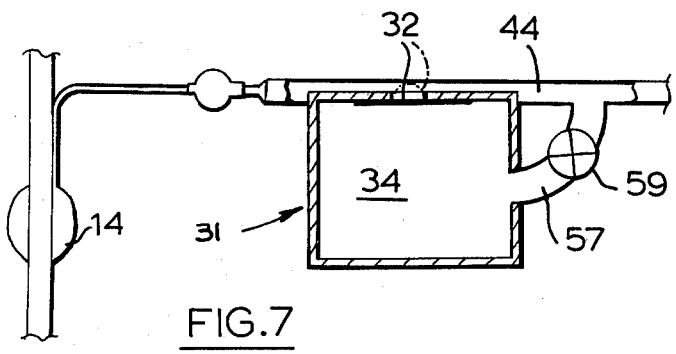

FIG. 7 of the drawings illustrates a still further modification in which like numerals are applied to like parts to those illustrated in FIG. 5 of the drawings. In this embodiment, a single passage 57 extends from the through passage 44 to the pressure chamber 34 and a closure valve 59 is located in the passage 57.

In use, the valve 59 is located in an open position to connect the through passage 44 with the pressure chamber 34. A pressure source is then applied to the open end of the through passage 44 and air is admitted at sufficient pressure to inflate the cuff 14 to achieve the required seal between the tracheal tube cuff and the tracheal wall as previously described. The pressure chamber 34 is simultaneously pressurized to the same pressure as the pressure applied to the cuff. The valve 59 is then moved to the closed position closing the passage 57 and the pressure source is then removed from the free end of the passage 44. The reduction in pressure in the through passage 44 caused by the removal of the pressure source causes the valve closure member 32 to extend to close the through passage 44. The pressure relief valve 31 then operates in the manner previously described. To deflate the cuff, the valve 57 is moved to the open position opening the communication between the pressure chamber 34 and the passage 44, thereby allowing the pressure chamber 34 to be depressurized. The valve closure member 32 then returns to its relaxed configuration and the passage 44 is automatically opened.

Figure 8:
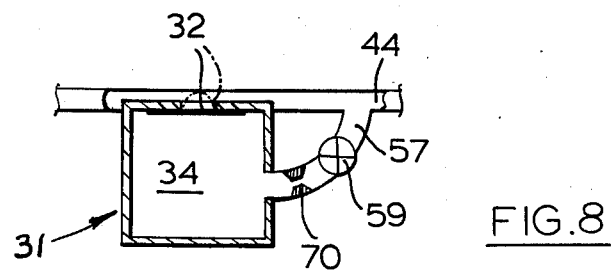

It will be understood that in each of the previous examples in which air is simultaneously supplied to pressurize the cuff 14 and to pressurize the pressure chamber 34, it may be necessary to include a restriction in the passage leading to the pressure chamber to ensure that the cuff is inflated to the required pressure before the pressure relief valve 31 moves to its closed position. FIG. 8 of the drawings illustrates a restriction 70 in the passage 57 of a pressure relief valve constructed in accordance with FIG. 7. The restriction 70 can be proportioned to ensure that the cuff 14 or any other inflatable system is properly inflated before the pressure chamber 34 is fully pressurized and may be located at any point along the length of the passage 57.

An alternative method of ensuring correct inflation may be to proportion the pressure chamber so that it has a volume which is so much greater than the expanded volume of the cuff and the tubes leading to the cuff to ensure that the cuff system is automatically inflated before the pressure chamber is inflated. If under such circumstance, the volume of air or gas from the pressure source entering the cuff system is equal to the volume of air or gas entering the pressure chamber, the pressure inside the pressure chamber will initially be less than the pressure in the cuff system during pressurization and thus the diaphragm 32 will not move to a position closing the through passage 44. After pressurization of the cuff 14 has been completed and the pressure in the cuff system and in the pressure chamber will equalize rapidly, the valve closure member 32 can be caused to move to the closed position as a result of a minor drop in pressure in the cuff system when the pressure source is removed.

If the passage connecting the pressure chamber 34 and the pressurizing source is of a smaller diameter than the passage 44 and the passage connecting the passage 44 to the cuff, the cuff can be inflated to the required pressure before the pressure chamber 34 is fully pressurized to cause the valve closure member 32 to move to the closed position. Thus, it will be seen that various systems may be developed for preventing closure of the valve closure member 32 before the cuff has been pressurized.

FIG. 9 of the drawings illustrates a further modification of the system of the present invention in which two pressure release valves 31a and 31b are used in association with a pressure system to control the pressurization and release of pressure from the system. The system to be pressurized may be a cuff 14 such as that previously described or any other pressure system used in medicine or in industrial applications. The valve 31a is positioned to close passage 44a and the valve 31b is positioned to close passage 44b. Passages 44a and 44b lead to the pressure system such as cuff 14. The passage 72 connects the pressure chamber 34a to the passage 44b and the valve 74 is located in the passage 72. Valve 88 is located in the passage 44b and downstream from the connection of the passage 72. Valve 52a is located in the passage 50a which opens into the pressure chamber 34a. Passage 58a opens from the passage 50a to atmosphere and a manometer 60a is located in passage 56a. The pressure relief valve 31b is constructed in the same manner as the pressure relief valve 31a with the like parts being identified by like numerals followed by the suffix "b".

With the valve 74 in a closed position and the valve 52a in the open position, the chamber 34a is pressurized by applying an inflating device to the passage 58a until a predetermined pressure is reached as measured by the manometer 60a. The valve closure member 32a will close the passage 44a when the pressure in the system is below the pressure in the pressure chamber 34a. When the chamber 34a has been pressurized to the required predetermined pressure, the valve 52a is closed and with the valve 88 in the closed position the valve 74 is opened. In order to pressurize the chamber 34b, the valve 52b is opened and a source of pressure is connected to the passage 58b. A predetermined pressure is applied to the pressure chamber 34b as measured by the manometer 60b. The pressure in the chamber 34b is higher than the pressure in the chamber 34a. The valve 52b is closed and the valve closure member 32b closes the passage 44b. The valve 88 is then moved to the open position. Thus, valves 52a and 52b are closed and valves 88 and 74 are open.

In use, the cuff 14 may be inflated by the application of an inflating syringe to the free end of the passage 44 in the same manner that the cuff 14 is inflated in the embodiment illustrated in FIG. 2. When the pressure in the system increases, the pressure in the chamber 34a will also increase with the result that there is no release of pressure by way of the pressure relief valve 31a. When the pressure in the system is higher than the pressure in chamber 34b, the valve closure member 32b will be moved to an open position to relieve pressure by way of pressure relief valve 31b.

From the foregoing, it will be apparent that a substantial number of systems can be developed in which a pneumatic pressure relief valve can be used in association with the pressure system of an inflatable cuff or a tracheal or endotracheal tube system. The pneumatically controlled pressure relief valve of the present invention has the advantage of being inflatable by inflation means compatible with equipment such as inflating syringes normally used for inflating cuffs and the like. The pneumatic pressure relief valve also has the advantage that it can be used with or without a manometer in order to set the relief pressure and it is unaffected by its orientation. It also has the advantage that the pressure chamber is of a substantial volume so that the deflection of the valve closure member from its closed position to its open position does not substantially increase the pressure in the pressure chamber. As a result, the valve of the present invention may be constructed so that it is extremely sensitive because the pressure variation in the pressure chamber between the open and closed positions of the valve is very small. In contrast in systems in which a bladder is located within the through passage of the valve and it is necessary to fully deflate the bladder to open the valve a considerable pressure variation is likely to result within the pressure system.

While in the embodiments of the invention described above reference is made to the inflation of a cuff of a tracheal or endotracheal tube, it will be noted that the cuff merely constitutes one pressure source which is to be regulated.

As shown in FIG. 10 of the drawings, the pressure source may be in the form of the expiratory limb 80 of a patient's breathing circuit. Under these circumstances, the chamber 34 is pressurized to a predetermined pressure with a manometer 60 measuring the predetermined pressure by way of the passage 56. Thus, the pressure relief valve of the present invention will provide a positive end expiratory pressure in a patient's breathing circuit.

In another application, as illustrated in FIG. 11 of the drawings, wherein the line 82 of the pressure system is connected by the arm 84 to a suction machine and the line 86 is connected to the suctioning catheter or the like for suctioning secretions, as for example in suctioning of the tracheal tube or in continuous suctioning of the gastrointestinal tract or a body cavity such as the pleural cavity. The pressure in the chamber 34 is a predetermined pressure which is applied as previously indicated. When an excessively low pressure occurs in the suctioning lines 84 and 86, the pressure relief valve will open to admit air through the line 82. As a result, the pressure relief device of the present invention may be used to prevent excessively low pressures in a suctioning system.

The tubular portion 30 and the walls of the pressure chamber 34 are preferably made from a transparent plastic material so that the operation of the valve can be visually observed by the operator.

In describing the preferred embodiments, the valve has been described as used in a number of medical application, it will, however, be apparent that the pressure relief valve of the present invention may be used in any number of industrial or commercial applications for controlling the pressure in any fluid conveying line. It will also be apparent that the fluid may not necessarily be air.

In the preferred embodiment described above, the valve passage which communicates between the pressure chamber 34 and the through passage 44 is illustrated as being of a circular configuration. Alternative configurations may, however, be employed to advantage in certain applications. For example, when the fluid in the through passage 44 is at a high pressure the valve passage may conveniently be of an oval shape as shown in FIG. 12a with the major axis 90 extending in the longitudinal direction of the through passage 44 and the minor axis 92 extending transversely of the through passage 44. In low pressure or negative pressure systems, the valve passage 44 may be of an oval configuration as shown in FIG. 12b with the major axis 90 extending transversely and the minor axis 92 extending longitudinally with respect to the through passage 44. In yet another variation, FIG. 12c, the valve passage may have its major axis 90 extending obliquely across the through passage 44. It should be noted that the valve passage, in negative pressure applications, should not have a major axis extending in the longitudinal direction of the through passage as the valve closure member would not necessarily collapse inwardly to open the through passage in such a construction.

From the foregoing, it will be apparent that the pneumatic valve of the present invention is of a simple construction and is simple to operate and maintain. The operation of the valve is unaffected by its position or by the position of the system to which it is connected in use. The valve may be used to maintain the pressure in the system at any predetermined level. The valve is capable of releasing pressures in excess of the preset pressure if the pressure in the system increases above the preset pressure. The valve can be regulated with ease and its function can be visually checked when it is constructed of a suitable transparent material. The generation of a positive end expiratory pressure in any clinical setting, such as in an operating room can be achieved with ease in an intubated patient. The valve may be used to regulate both positive and negative pressures. Two or more pneumatic valves according to the present invention may be used in any system to permit the system to operate within a wide pressure range as described in FIG. 9 of the drawings. Also as indicated in the drawings various systems can be developed for providing simultaneous pressurization of the system and the pressure chamber.

These and other applications of the pneumatic valve of the present invention will be apparent to those skilled in the art.

For example, two or more of the penumatic valves of the present invention may be connected in series or in parallel in order to increase the reliability of any of the systems described above.

What I claim as my invention is:

1. A self-contained automatic penumatic vent valve comprising;
   (a) a body,
   (b) a through passage opening through said body, said through passage having a longitudinally extending first side wall which is arcuate in shape in a direction transverse to its longitudinal extent,
   (c) an enclosed pressure chamber formed in said body and disposed outwardly from said through passage,
   (d) a valve passage extending between said pressure chamber and said through passage, said valve passage having a first end disposed opposite and opening toward said first side wall of said through passage,
   (e) a flexible valve closure member mounted in said body and extending across said first end of said valve passage to close said valve passage, said flexible closure member being disposed opposite said first side wall of said through passage in a face-to-face relationship therewith and being extendable from a first position in which it is spaced from said first side wall to permit free flow of fluid through said through passage to a second position in which it extends into engagement with said first side wall to close said through passage in response to variations in the differential pressure between the pressure in said pressure chamber and the pressure in said through passage,
   (f) a single input passage means opening into said pressure chamber for admitting air under pressure to and venting air from said pressure chamber,
   (g) valve means in said single input passage which is operable for selectively opening and closing said input passage whereby when said valve is closed it completely isolates said pressure chamber such that after pressurizing said pressure chamber, said valve may be closed and said pneumatic vent valve may operate automatically to open and close said through passage as required in use.

2. A pneumatic valve as claimed in claim 1 wherein said through passage has a semi-circular cross-sectional configuration, said flexible valve closure member comprising a flexible diaphragm extending across said first end of said valve passage in a substantially relaxed configuration when in said first position and being elastically expandable in response to air pressure in said pressure chamber to move to said second position.

3. A pneumatic valve as claimed in claim 1 wherein said pressure chamber has a volumetric capacity which is substantially greater than the increase in its volume caused by movement of said flexible valve closure member from said first position to said second position so that said valve closure member may be displaced from said second position to permit venting through said through passage without causing a substantial increase in pressure in said pressure chamber.

4. In an inflatable cuff system of a tracheal or endotracheal tube having an inflation passage communicating with the inflatable cuff, the improvement of: an automatic pneumatic vent valve in said inflation passage comprising;
(a) a body,
(b) a through passage opening through said body, said through passage having a longitudinally extending first side wall which is arcuate in shape in a direction transverse to its longitudinal extent, said through passage having an input end and an output end, the output end communicating with said inflation passage and the input end being releasably connectible to a source of inflating medium for the inflatable cuff,
(c) a pressure chamber formed in said body and disposed outwardly from said through passage,
(d) a valve passage extending between said pressure chamber and said through passage, said valve passage having a first end disposed opposite and opening toward said first side wall of said through passage,
(e) a flexible valve closure member mounted in said body and extending across said first end of said valve passage to close said valve passage, said flexible closure member being disposed opposite said first side wall of said through passage in a face-to-face relationship therewith and being extendable from a first position in which it is spaced from said first side wall to permit free flow of fluid through said through passage to a second position in which it extends into engagement with said first side wall to close said through passage in response to variations in the differential pressure between the pressure in said pressure chamber and the pressure in said through passage,
(f) an input passage opening into said pressure chamber for admitting air to and venting air from said pressure chamber,
(g) a valve in said input passage which is operable for selectively opening and closing said input passage whereby when said valve is closed it completely isolates said pressure chamber such that after pressurizing said pressure chamber said valve may be closed and said pneumatic vent valve may operate automatically to open and close said through passage as required in use.

5. An inflatable cuff system as claimed in claim 4 wherein said valve closure member comprises a flexible diaphragm having a pair of oppositely disposed side faces, one of said side faces being exposed to said pressure chamber and the other of said side faces being exposed to said inflation passage whereby said flexible diaphragm may be extended into said inflation passage to close said inflation passge when the pressure in said pressure chamber exceeds the pressure in said inflation passage and whereby said valve closure member may yield to open said inflation passage when the pressure in said inflation passage exceeds the pressure in said pressure chamber.

6. An inflatable cuff system as claimed in claim 4 including first manometer mounting passage means communicating with said input passage means whereby the air pressure applied to said pressure chamber may be measured.

7. An inflatable cuff system as claimed in claim 4 wherein said input passage means communicates with said through passage whereby said pressure chamber may be pressurized as said cuff is pressurized by way of said inflation passage.

8. An inflatable cuff system as claimed in claim 7 wherein said input passage means communicates with the inflation passage downstream from said pneumatic valve.

9. In an inflatable cuff system of a tracheal or endotracheal tube having an inflation passage communicating with the inflatable cuff, the improvement of: an automatic pneumatic vent valve in said inflation passage comprising;
(a) a body,
(b) a through passage opening through said body, said through passage having a longitudinally extending first side wall which is arcuate in shape in a direction transverse to its longitudinal extent, said through passage having an input end and an output end, the output end communicating with said inflation passage and the input end being releasably connectible to a source of inflating medium for the inflatable cuff,
(c) a pressure chamber formed in said body and disposed outwardly from said through passage,
(d) a valve passage extending between said pressure chamber and said through passage, said valve passage having a first end disposed opposite and opening toward said first side wall of said through passage,
(e) a flexible valve closure member mounted in said body and extending across said first end of said valve passage to close said valve passage, said flexible closure member being disposed opposite said first side wall of said through passage in a face-to-face relationship therewith and being extendable from a first position in which it is spaced from said first side wall to permit free flow of fluid through said through passage to a second position in which it extends into engagement with said first side wall to close said through passage in response to variations in the differential pressure between the pressure in said pressure chamber and the pressure in said through passage,
(f) an input passage opening into said pressure chamber for admitting air to and venting air from said pressure chamber,
(g) a valve in said input passage which is operable for selectively opening and closing said input passage whereby when said valve is closed it completely isolates said pressure chamber such that after pressurizing said pressure chamber said valve may be closed and said pneumatic vent valve may operate automatically to open and close said through passage as required in use,
(h) passage means communicating between said input passage of said pressure chamber and said through passage between said input end of said through passage and said flexible valve closure member whereby said cuff and said pressure chamber may be pressurized by way of said input passage of said through passage.

* * * * *